US00PP37785P2

(12) United States Plant Patent
Grosser

(10) Patent No.: US PP37,785 P2
(45) Date of Patent: Oct. 20, 2026

(54) GRAPEFRUIT-LIKE HYBRID PLANT NAMED 'C2-5-3'

(50) Latin Name: ***Citrus* sp.**
Varietal Denomination: C2-5-3

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/376,091

(22) Filed: Oct. 31, 2025

(51) Int. Cl.
*A01H 5/08* (2018.01)
*A01H 6/78* (2018.01)

(52) U.S. Cl.
USPC ..... Plt./201

(58) Field of Classification Search
USPC ..... Plt./201
CPC . A01H 5/08; A01H 5/00; A01H 6/785; A01H 6/78
See application file for complete search history.

(56) References Cited

U.S. PATENT DOCUMENTS

PP27,744 P3 3/2017 Grosser

OTHER PUBLICATIONS

Grosser 2021 Two Unique Fresh Fruit Selections Approved for Release, UF/IFAS Citrus Research Summaries, retrieved on Feb. 10, 2026 at https://crec.ifas.ufl.edu/media/crecifasufledu/citrus-research/docs/expo2021/growers-booklet/CREC_Research-Summeries-2021-39.pdf, p. 39. (Year: 2021).*
Grosser 2023 What can Variety Improvement Do to Solve the Brix Crisis in Florida NFC? And, New Graprefruit Opportunities! retrieved on Feb. 10, 2026 at New-UFIFAS-Citrus-Scions-and-Rootstocks.pdf, 32 pp. (Year: 2023).*

* cited by examiner

*Primary Examiner* — June Hwu
(74) *Attorney, Agent, or Firm* — Koenig IP Works, PLLC; Katherine Koenig

(57) ABSTRACT

A new and distinct grapefruit-like hybrid cultivar plant named 'C2-5-3', characterized by early development of a brix/acid ratio of 12-15 (in September in Florida), resulting in fruit having a sweet, grapefruit-like flavor. Additionally, fruit of 'C2-5-3' could be packed early, in September and October. The new cultivar 'C2-5-3' also demonstrates HLB tolerance.

12 Drawing Sheets

Genus and species: *Citrus* sp.
Cultivar denomination: 'C2-5-3'.

BACKGROUND OF THE NEW CULTIVAR

The present invention relates to a new and distinct cultivar of grapefruit-like hybrid, botanically known as *Citrus* sp., and hereinafter referred to by the name 'C2-5-3'. *Citrus* sp. is a member of Rutaceae.

The new Grapefruit-like hybrid cultivar 'C2-5-3' is a triploid progeny from an interploid cross of 'Hirado Buntan Pink' pummelo (*Citrus grandis* Osbeck) x [somatic hybrid of 'Succari' sweet orange (*Citrus sinensis* L. Osbeck) + 'Hirado Buntan Pink' pummelo]. 'Hirado Buntan Pink' and 'Succari' are not patented. It is one of several triploid hybrids from this cross that produces early-maturing, pink-fleshed, and delicious fruit. This hybrid is essentially ⅔pummelo and ⅓sweet orange. This new cultivar has been asexually reproduced via budwood grafting, as is standard for citrus cultivars. The original 'C2-5-3' tree, grafted to 'Swingle' citrumelo (not patented), is approximately 15 years old and is located in Lake Alfred, Florida. Even though grafted to 'Swingle' citrumelo rootstock, which is considered to be susceptible to HLB (huanglongbing or citrus greening disease), the original tree still exhibits reasonably good health, while many surrounding trees (other citrus genotypes) have declined or died due to HLB. Trueness to type was validated on trees propagated by grafting onto 'UFR-3' rootstock (U.S. Plant Pat. No. 27,744) and planted in Lake Alfred, Florida (fruiting trees are now 4 years old).

Plant Breeder's Rights for this cultivar have not been applied for. The new grapefruit-like hybrid cultivar 'C2-5-3' has not been made publicly available more than one year prior to the filing of this application.

SUMMARY OF THE INVENTION

The new grapefruit-like hybrid cultivar 'C2-5-3' has not been observed under all possible environmental conditions. The phenotype of the new cultivar may vary with variations in environment and cultural practices such as temperature, light intensity, fertilization, irrigation, and application of plant growth regulators without any change in genotype.

Fruit of the new cultivar 'C2-5-3' can reach a brix/acid ratio of 12-15 in September in Florida, resulting in a sweet, grapefruit-like flavor before any standard Florida grapefruit cultivars are ripe. Although the fruit exhibits a grapefruit-like flavor, the flavor is sweeter and less bitter than standard grapefruit, which gives it potential to appeal to a wider audience than standard grapefruit. Standard grapefruit packing in Florida generally gets underway in November, with the industry generally packing low-ratio fruit. Fruit of 'C2-5-3' could easily be packed in September and October, providing new marketing opportunities to Florida grapefruit growers and packers. The new cultivar 'C2-5-3' has displayed better HLB tolerance than standard grapefruit cultivars, as the original tree of the new cultivar has survived HLB and has remained productive whereas all nearby standard cultivar grapefruit trees have severely declined or died. HLB-symptomatic fruit have not been observed. Citrus canker, which is prevalent in Lake Alfred, Florida, has not been as problematic on the original 'C2-5-3' tree as it has been on nearby standard grapefruit, suggesting a high level of tolerance to this disease that remains highly problematic to the Florida grapefruit industry. There are no data supporting long-term field performance or yield, although the original 'C2-5-3' tree has repeated for good yields the past several seasons. Fruit of the new cultivar 'C2-5-3' is expected to be suited for the fresh market.

Plants of the new grapefruit-like hybrid cultivar 'C2-5-3' cannot currently be compared to the parent interploidy cross of 'Hirado Buntan Pink' pummelo (*Citrus grandis* Osbeck) x [somatic hybrid of 'Succari' sweet orange (*Citrus sinensis* L. Osbeck) + 'Hirado Buntan Pink' pummelo] because the original parent tree died and new plants of the parent cross are currently available only as young trees that are not yet fruiting. However, fruit of 'Hirado Buntan Pink' is quite seedy when cross pollinated, whereas fruit from the new cultivar 'C2-5-3' is seedless but can contain some large seed traces. Further, fruit of the new cultivar 'C2-5-3' is smaller and less tart than, and matures about one month earlier than, fruit of 'Hirado Buntan Pink'. Plants of the new grapefruit-like hybrid cultivar 'C2-5-3' can be compared to 'Pink Marsh' grapefruit. In side-by-side comparisons conducted in Lake Alfred, Florida, plants of the new cultivar 'C2-5-3' differed from plants of 'Pink Marsh' in the following characteristics:

1. Fruit of 'C2-5-3' has darker pink flesh color than 'Pink Marsh', especially close to the segment walls.
2. Fruit of 'C2-5-3' has higher Brix in September/October than 'Pink Marsh'.
3. Fruit of 'C2-5-3' has higher Brix/Acid Ratio and sweeter flavor in September/October than 'Pink Marsh'.

DESCRIPTION OF THE FIGURES

The accompanying photographs (as shown in FIGS. 1-14) illustrate the overall appearance of the new grapefruit-like hybrid cultivar 'C2-5-3'. These photographs show the colors as true as can be reasonably obtained in colored reproductions of this type. Colors in the photographs may differ slightly from the color values cited in the detailed botanical description, which accurately describe the colors of the new cultivar.

DETAILED BOTANICAL DESCRIPTION OF THE CULTIVAR

Figure 1:
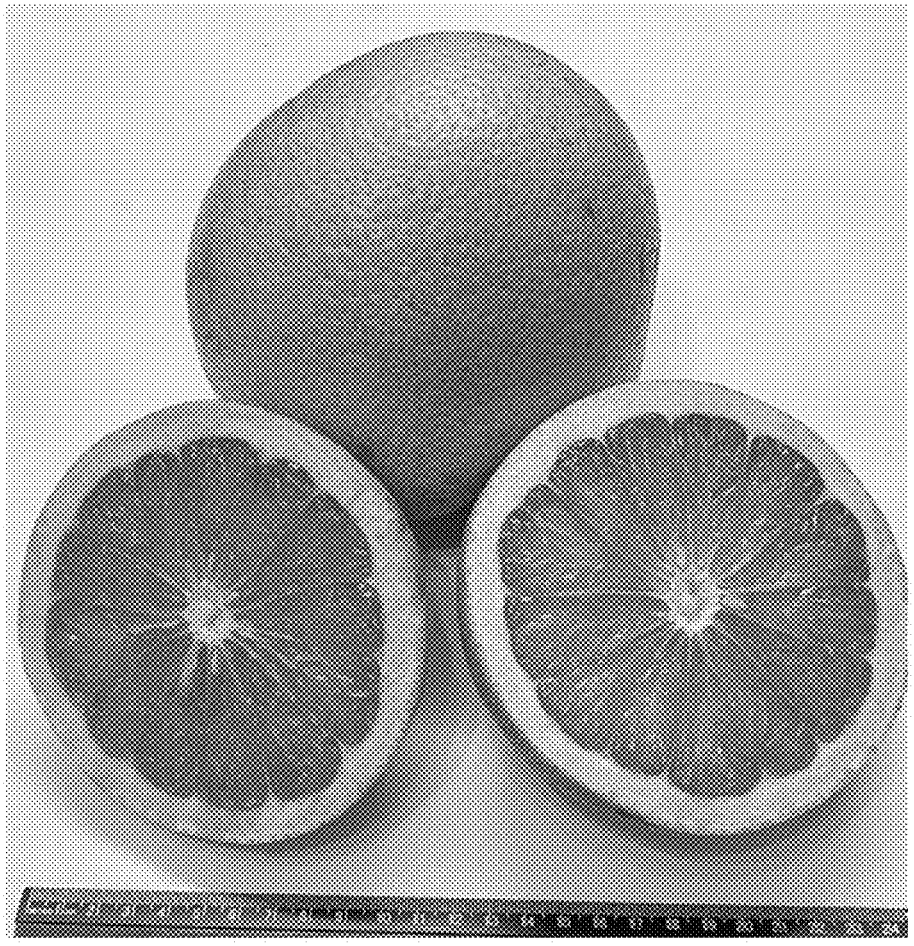
FIG. 1 shows cut and whole fruit of the new cultivar 'C2-5-3', with a ruler shown for size reference.
Figure 2:
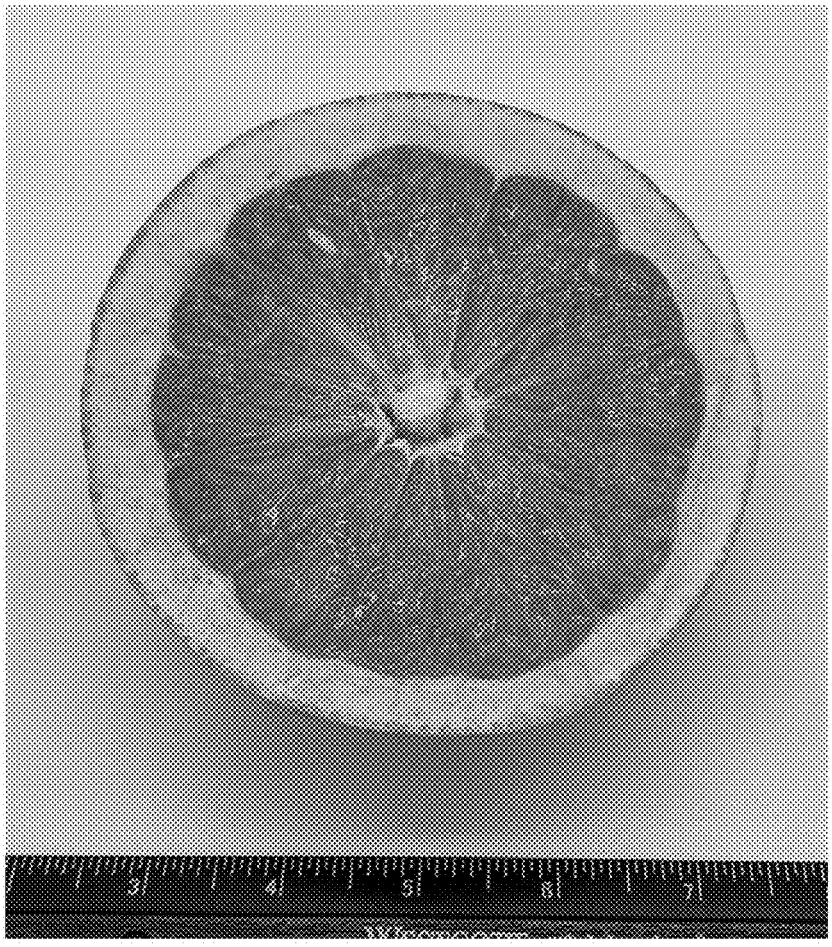
FIG. 2 shows a cut fruit of the new cultivar 'C2-5-3' (transverse cut), with a ruler shown for size reference.
Figure 3:
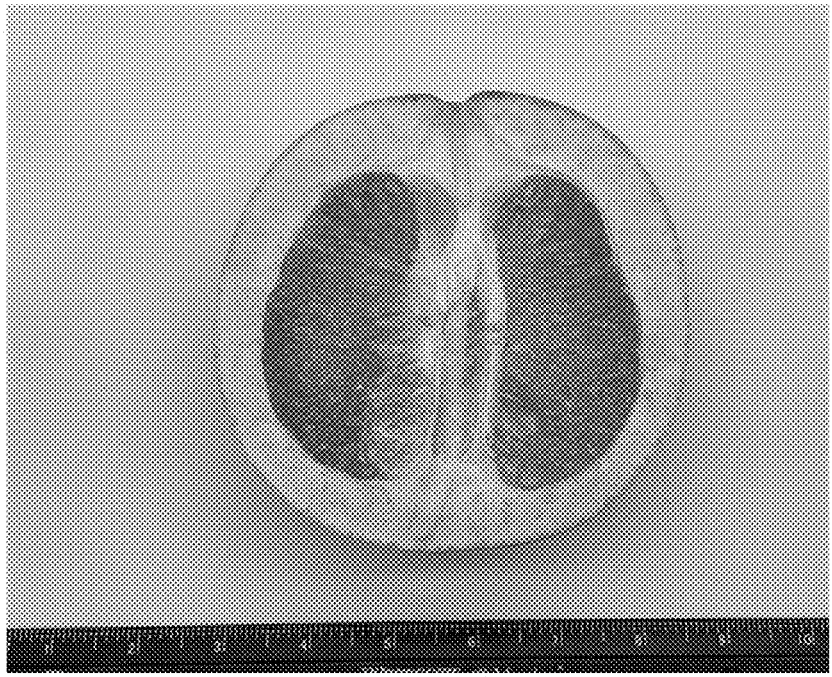
FIG. 3 shows a cut fruit of the new cultivar 'C2-5-3' (longitudinal cut), with a ruler shown for size reference.
Figure 4:
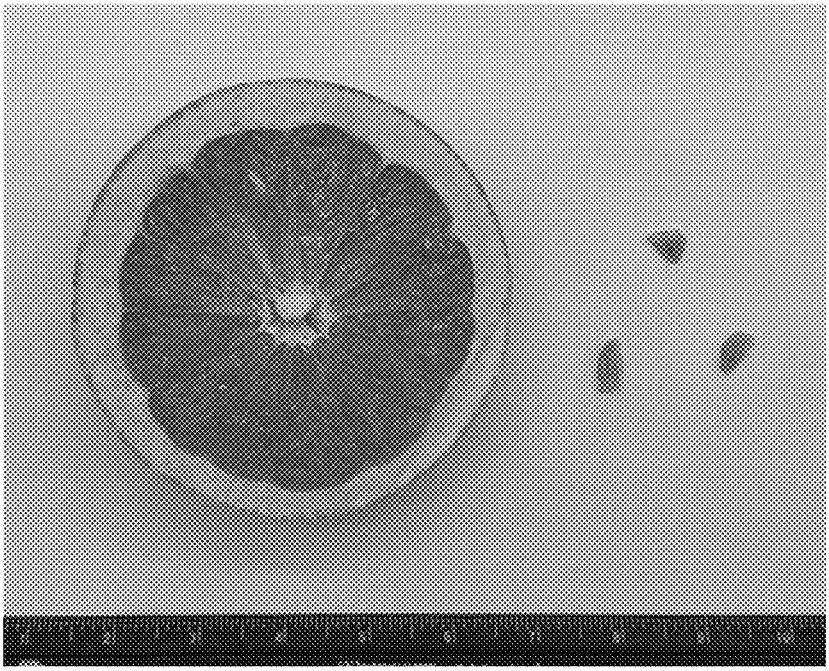
FIG. 4 shows a cut fruit of the new cultivar 'C2-5-3' (transverse cut) and seeds, with a ruler shown for size reference.
Figure 5:
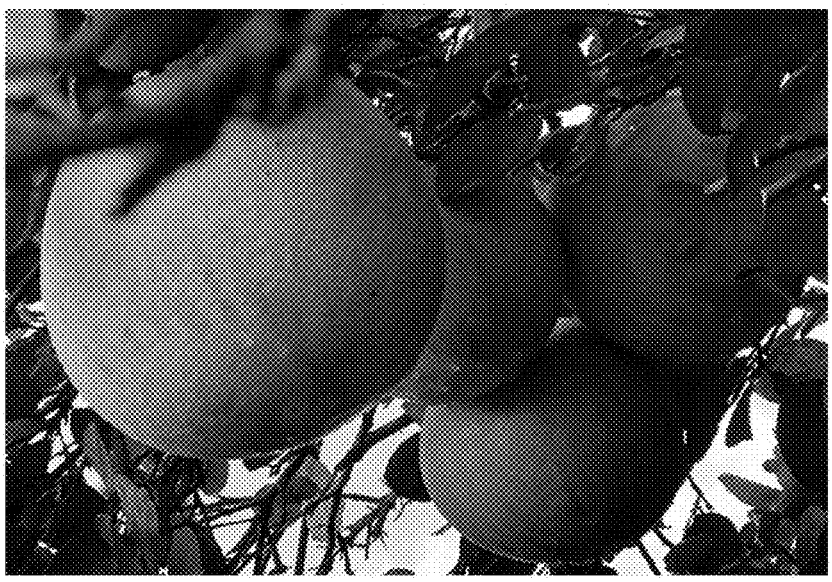
FIG. 5 shows a close-up view of fruit of the new cultivar 'C2-5-3' on the tree.
Figure 6:
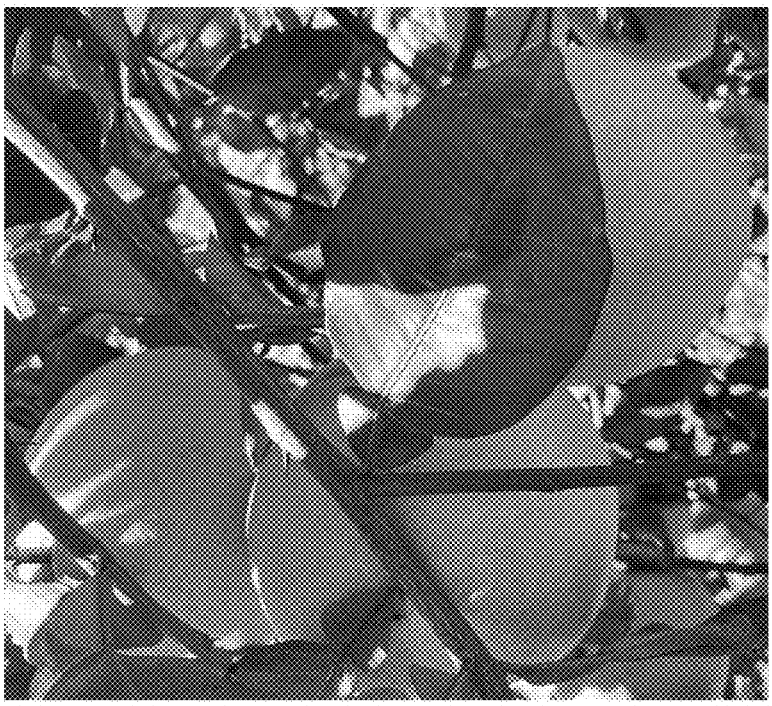
FIG. 6 shows a close-up view of fruit of the new cultivar 'C2-5-3' on the tree.
Figure 7:
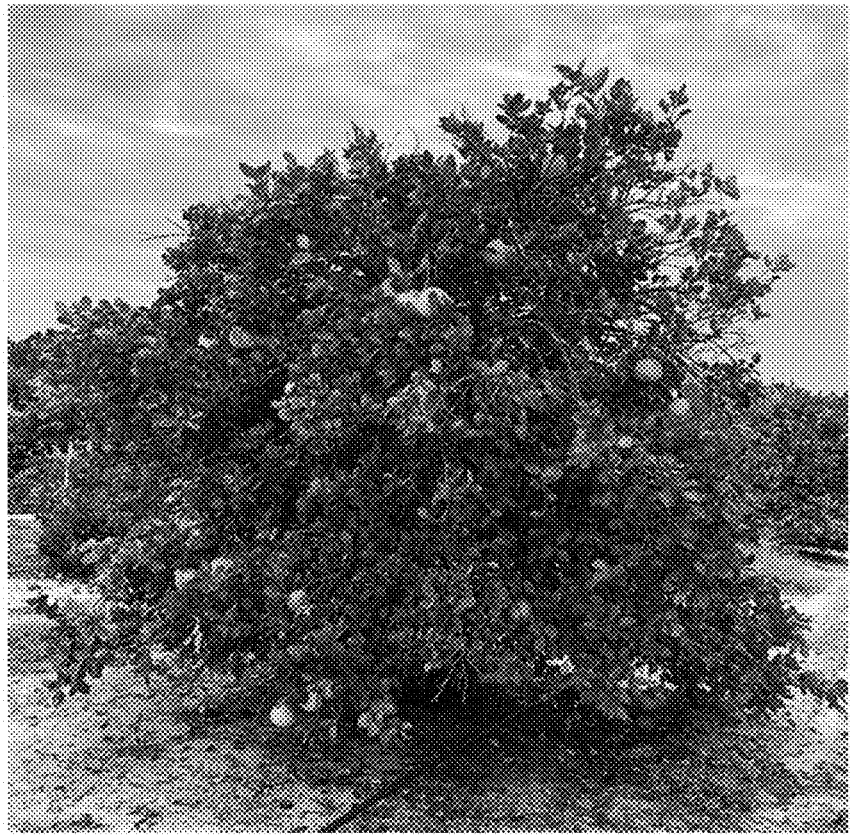
FIG. 7 shows the overall tree growth habit of the new cultivar 'C2-5-3'.
Figure 8:
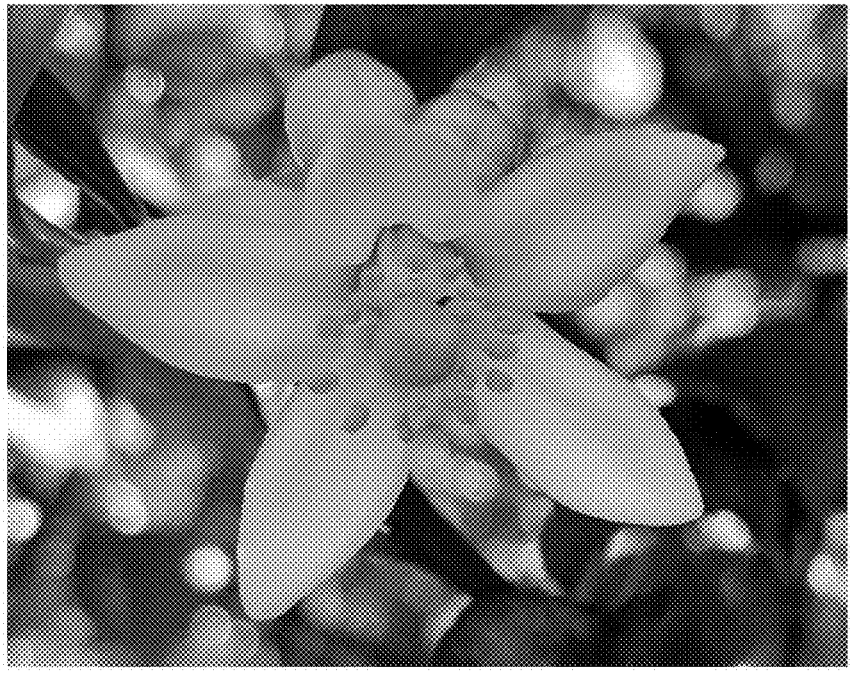
FIG. 8 shows a close-up view of a flower of the new cultivar 'C2-5-3' on the tree.
Figure 9:
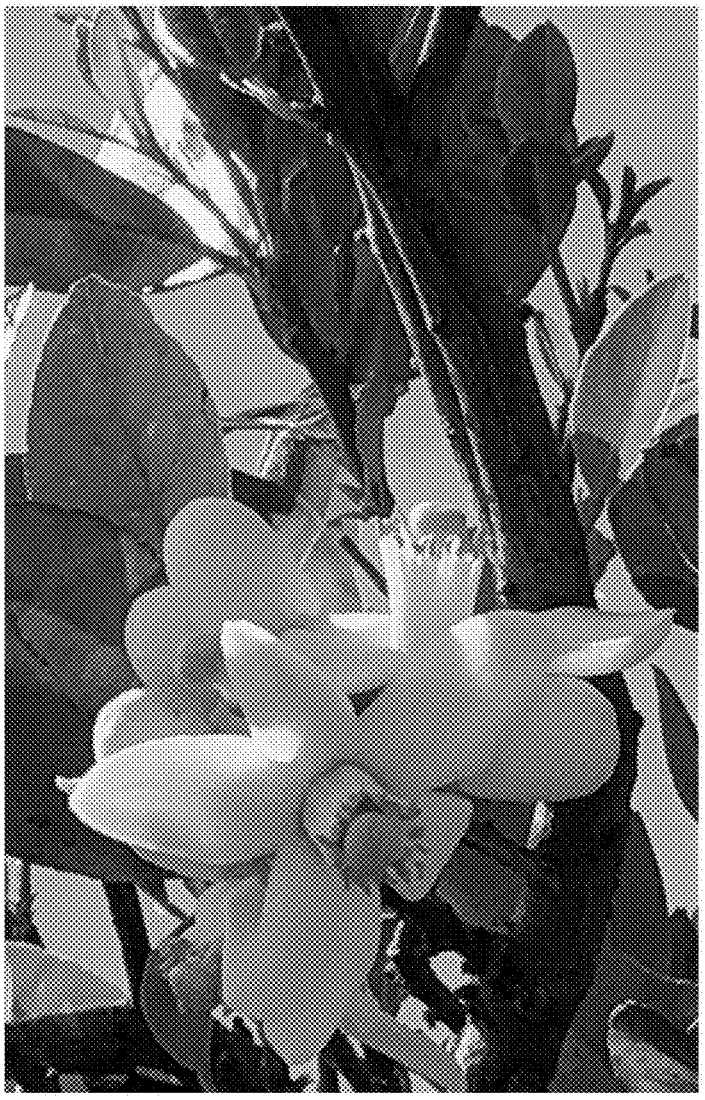
FIG. 9 shows a close-up view of a cluster of flowers of the new cultivar 'C2-5-3' on the tree.
Figure 10:
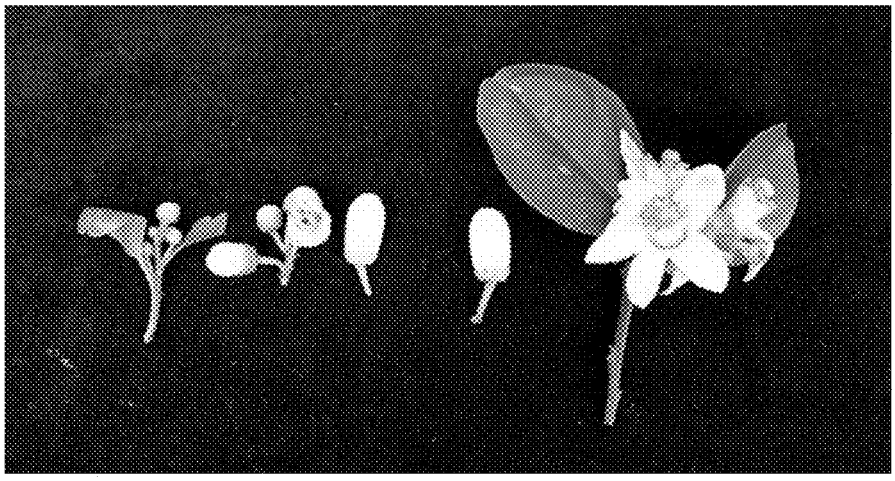
FIG. 10 shows leaves and flowers of the new cultivar 'C2-5-3' in different developmental stages.
Figure 11:
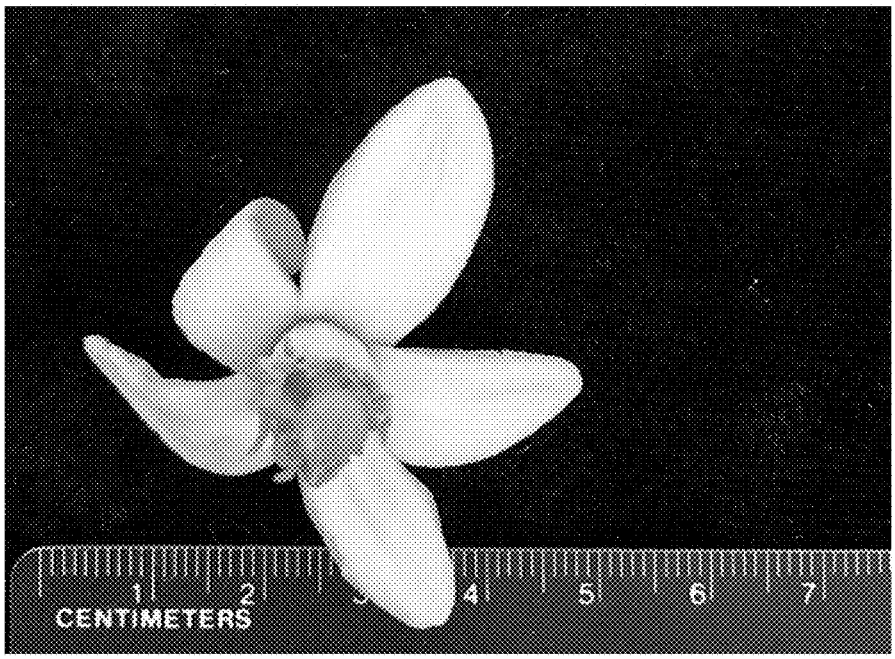
FIG. 11 shows a close-up view of a flower of the new cultivar 'C2-5-3', with a ruler shown for size reference.
Figure 12:
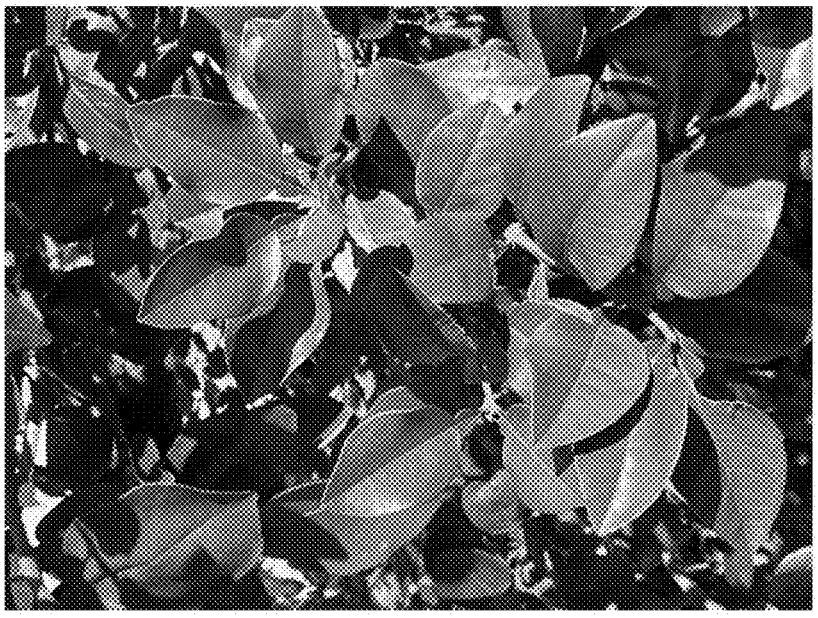
FIG. 12 shows a close-up view of leaves of the new cultivar 'C2-5-3' on the tree.
Figure 13:
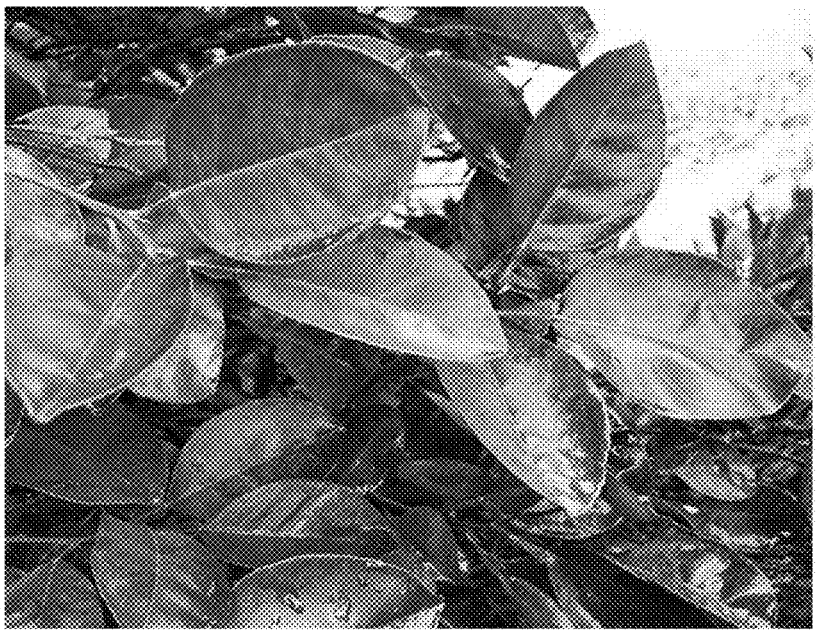
FIG. 13 shows a close-up view of leaves of the new cultivar 'C2-5-3' on the tree.
Figure 14:
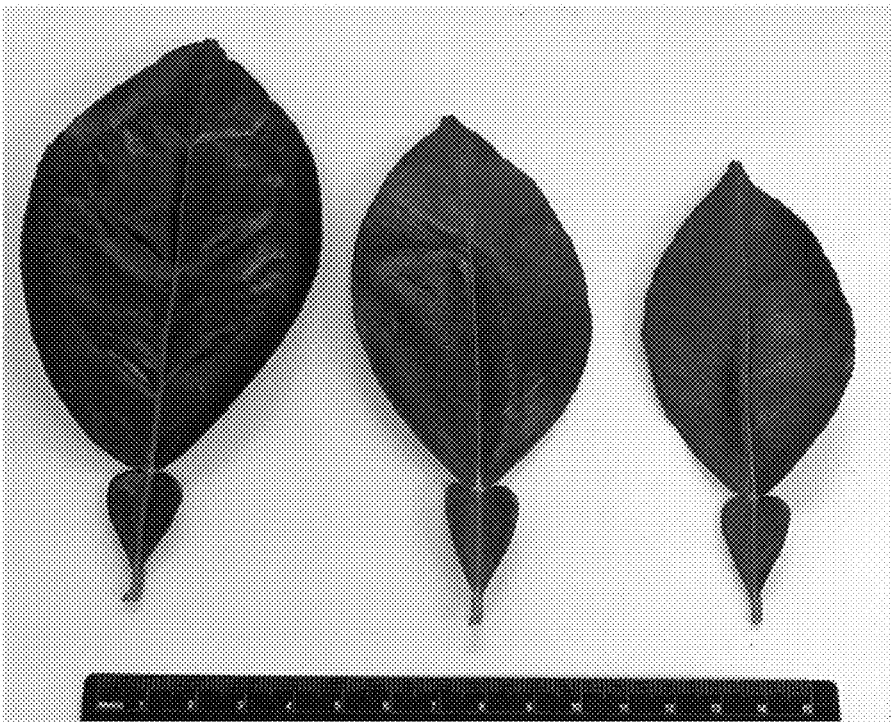
FIG. 14 shows fully-expanded leaves of the new cultivar 'C2-5-3', with a ruler shown for size reference.

In the following description, color references are made to The Royal Horticultural Society (R.H.S.) Colour Chart, 1986 Edition and 2001 Edition (where noted), except where general terms of ordinary dictionary significance are used.

Botanical Description

Botanical classification:

*Family.*—Rutaceae.

*Botanical name.*—*Citrus* sp. (*Citrus grandis* Osbeck x [somatic hybrid (*Citrus sinensis* L. Osbeck) + (*Citrus grandis* Osbeck).

*Common name.*—Grapefruit-like hybrid.

*Cultivar.*—'C2-5-3'.

Parentage: The new grapefruit-like hybrid cultivar 'C2-5-3' is a triploid progeny from an interploid cross of 'Hirado Buntan Pink' pummelo (*Citrus grandis* Osbeck) (female parent) x [somatic hybrid of 'Succari' sweet orange (*Citrus sinensis* L. Osbeck) + 'Hirado Buntan Pink' pummelo] (male parent).

Tree:

*Ploidy.*—Triploid.

*Size.*—Medium. Width across row: 3.7 meters on average. Width down row: 3.8 meters on average.

*Tree height.*—3.5 meters on average.

*Tree canopy.*—3.4 meters in diameter on average.

*Vigor.*—Moderate.

*Density.*—Canopies are moderately dense.

*Tree shape (form).*—Obloid shape.

*Growth habit (current season).*—Tree with mostly upright growth and with lateral growth branches and lower medium angle.

Trunk:

*Trunk diameter.*—8.5 cm on average at 30 cm above the ground.

*Trunk texture.*—Medium rough.

*Trunk bark color.*—RHS 199 A (Grey-Brown Group).

Branches:

*Branch length.*—2.7 meters on average.

*Branch diameter.*—3.9 cm on average.

*Crotch angle.*—Acute with an average angle of 80-85 (less than 90 degrees).

*Branch texture: Medium rough with long spines.*

*Branch color.*—RHS 199 C (Grey-Brown Group).

*Spine size.*—2.1 cm in length and 3 mm in diameter on average.

*Spine color.*—R.H.S. N 199 B (greyed brown) and some with RHS 139 A (green), depending on the branch age (The Royal Horticultural Society (R.H.S.) Colour Chart, 2001 Edition).

Leaves:

*Length.*—125 mm on average.

*Width.*—75 mm on average.

*L/W ratio.*—1.66 on average. Thickness: Slightly thicker than most diploid citrus cultivars, typical of triploids. Type: Simple (unifoliate). Shape: Elliptical. Apex: Retuse. Base: Acute. Margin: Moderately dentate. Surface: Upper surface: Smooth. Lower surface: Medium veins that are pinnately netted. Color: Upper surface (adaxial): RHS N 137A (Green Group) (The Royal Horticultural Society (R.H.S.) Colour Chart, 2001 Edition). Upper surface, venation: RHS 143C (Green Group) Lower surface (abaxial): RHS 139 B (Green Group). Lower surface, venation: RHS 144B (Green Group). Petiole: Shape and attachment: Brevipetiolate; petiole is shorter than leaf lamina. Junction between petiole and lamina: Articulate. Shape (petiole wing): Obovate with narrow end at the base. Length: 20-25 mm on average. Width: 22-25 mm on average. Color: R.H.S. N 137 A (Green Group) (The Royal Horticultural Society (R.H.S.) Colour Chart, 2001 Edition).

Flowers:

*Type.*—Hermaphrodite.

*Flowers bearing.*—Single or cluster. Branches have flowers grown in clusters. Each cluster consists of 3-6 flowers. Individual flowers grow from leaf terminals and leaf axillaries.

*Flower diameter.*—Fully open flowers have an average diameter of 38 mm.

*Flower depth.*—22 mm on average.

*Flower blooming period.*—First bloom: Generally mid-March in central Florida. Full bloom: Generally late-March in central Florida.

*Flowering habit.*—Flowers once per year.

*Fragrance.*—Fragrant: zesty and floral.

*Flower buds' size.*—Length: Initial visible flower bud: 2.5 mm on average. Mature flower bud, before opening: 26 mm on average. Diameter: Initial visible flower bud: 2.2 mm on average. Mature flower bud, before opening: 6.7 mm on average. Flower bud shape: Initial visible flower bud: Round dome shape. Mature flower bud: Elongated olive shape. Flower bud color: Initial visible flower bud: RHS 144 A (yellow-green). Mature flower bud: RHS NN 155 A (white) RHS N155A (White Group) for mature buds.

Reproductive organs:

*Fertility.*—Self-fertile.

*Petals.*—Number (per flower): 5. Petal length: 25 mm on average. Petal width: 12 mm on average. Petal shape: Flat spatula shape. Apex shape: Smooth with obtuse angle. Base shape: Obtuse.

*Petal color: Upper Surface: RHS* 155 B (White Group). Lower surface: R.H.S. N155A (White Group). Margin: Smooth.

*Sepal.*—Number (per flower): 5. Shape: Delta-shaped with acute angle at apex. Some sepals have a flat angle. Length: 7 mm on average. Width: 5 mm on average. Apex shape: Acute angle at apex. Margin: Smooth.

*Color.*—Upper surface: RHS 157C (green white). Lower surface: RHS 157B (green white).

*Pedicel.*—Length: 13 mm on average. Diameter: 2 mm on average. Color: RHS 144 B (yellow green).

*Stamen.*—Number: 29 per flower on average. Length: 15 mm on average.

*Anther.*—Length: 3.2 mm on average. Width: 2 mm on average. Color: RHS 13A (Yellow Group). Pollen color (general): RHS 13 B (Yellow Group).

*Pistil.*—Number (per flower): 1. Length: 7 mm on average. Color: RHS 154 B (yellow green). Style length: 13 mm on average. Style diameter: 2.1 mm on average. Style color RHS: 144 B (yellow green). Ovary shape: Oval shape.

*Ovary diameter.*—4 mm on average.

*Ovary color.*—RHS 142 B (green).

Fruit:

*Size.*—Uniform.

*Average weight* (*per individual fruit*).—750 grams.

*Length.*—13.2 cm on average.

*Diameter.*—12.1 cm on average.

*Shape.*—Spherical.

*Shape* (*cross-section*).—Round.

*Apex.*—Round.

*Base.*—Round.

*Depression at fruit stalk end.*—Present, but not deep.

*Harvest.*—Date of first pick: Usually the first of September in Florida. Date of last pick: End of October in Florida.

*Fruit stem.*—Length: 2.1 mm on average. Diameter: 4 mm on average. Color RHS: 147 B (yellow green).

*Rind.*—Adherence: Adherence of albedo (mesocarp) to flesh (endocarp) is medium. Thickness: Thick; 12-15 mm on average. Texture: Firm with excellent flavor. Surface texture: Smooth. Color: Flavedo (epicarp): RHS 1A (Green-Yellow Group) when the fruit is totally mature, but coloration with RHS 170 C (Greyed Orange Group) in some parts of the rind may occur. Albedo (mesocarp): RHS 27 B (Orange Group). Style end: Closed. Rind oil cell density: 45-50 cell/square cm on average. Oil Gland Size: Large size, 2 mm on average.

*Core diameter.*—15 mm on average.

*Flesh.*—Number of segments: 13 on average. Segment length: 9.5 cm on average. Segments width: 5.2 cm on average. Juice: Abundant (much juicier than early season grapefruit). Color: RHS 171A (Greyed-Orange Group) near the albedo and RHS 20A (Yellow-Orange Group) toward the core. Texture: Soft to medium. Vesicles: Thick. Length: 12 mm on average. Diameter: 5 mm on average.

*Juice quality* (*mid-September*).—Brix: 11. Acidity (average): 0.9%. Ratio: 12.2 on average (reached 15 one season). Juice color: USDA orange juice color system score of 35. Lb solid/box: Not available.

*Seeds.*—Type: Seedless; some fruits have a few shriveled seeds (2-3), possibly from cross pollination.

Resistance to diseases: The original tree of the new cultivar 'C2-5-3' has been positive for HLB for approximately 10 years. HLB caused some branch dieback, but tree health has gradually improved since the consistent application of supplemental controlled-release fertilizer containing an enhanced micronutrient package. Overall, the new cultivar has demonstrated tolerance to HLB and citrus canker that is much better than that of standard grapefruit.

What is claimed is:

1. A new and distinct cultivar of grapefruit-like hybrid plant named 'C2-5-3' as illustrated and described herein.

* * * * *